United States Patent
Danielsson et al.

(10) Patent No.: US 9,841,514 B2
(45) Date of Patent: Dec. 12, 2017

(54) X-RAY DETECTOR ARRANGEMENT

(71) Applicant: Prismatic Sensors AB, Stockholm (SE)

(72) Inventors: Mats Danielsson, Taby (SE); Staffan Karlsson, Bromma (SE)

(73) Assignee: PRISMATIC SENSORS AB, Stockholm (SE)

( * ) Notice: Subject to any disclaimer, the term of this patent is extended or adjusted under 35 U.S.C. 154(b) by 0 days.

(21) Appl. No.: 15/241,655

(22) Filed: Aug. 19, 2016

(65) Prior Publication Data
US 2017/0090046 A1    Mar. 30, 2017

Related U.S. Application Data

(60) Provisional application No. 62/232,051, filed on Sep. 24, 2015.

(51) Int. Cl.
| | | |
|---|---|---|
| *G01T 1/24* | (2006.01) | |
| *A61B 6/00* | (2006.01) | |
| *A61B 6/03* | (2006.01) | |
| *G01T 1/29* | (2006.01) | |

(52) U.S. Cl.
CPC ............ *G01T 1/242* (2013.01); *A61B 6/032* (2013.01); *A61B 6/4208* (2013.01); *A61B 6/4233* (2013.01); *A61B 6/4266* (2013.01); *G01T 1/2985* (2013.01)

(58) Field of Classification Search
CPC ....... A61B 6/032; A61B 6/4208; A61B 6/035; G01T 1/242; G01T 1/1614; G01T 1/24; G01T 1/1642; G01T 1/202
USPC .................................................. 250/370.09
See application file for complete search history.

(56) References Cited

U.S. PATENT DOCUMENTS

| | | | | |
|---|---|---|---|---|
| 4,438,164 A | * | 3/1984 | Pfeifer .................. | G03B 42/04 206/449 |
| 4,499,381 A | * | 2/1985 | Bauer ..................... | G03C 5/17 250/483.1 |
| 5,391,879 A | * | 2/1995 | Tran ...................... | G01T 1/2018 250/367 |
| 6,510,195 B1 | * | 1/2003 | Chappo ................. | G01T 1/2018 250/208.1 |
| 6,808,806 B2 | * | 10/2004 | Phillips ................. | B05D 5/061 106/456 |
| 7,212,604 B2 | * | 5/2007 | Tkaczyk ............... | G01T 1/2985 378/19 |
| 7,696,481 B2 | * | 4/2010 | Tkaczyk ............... | G01T 1/2018 250/363.02 |
| 8,183,535 B2 | | 5/2012 | Danielsson et al. | |
| 2002/0182383 A1 | * | 12/2002 | Phillips ...................... | C08J 7/04 428/199 |
| 2005/0161609 A1 | * | 7/2005 | Heismann .............. | A61B 6/032 250/370.09 |

(Continued)

OTHER PUBLICATIONS

M. Danielsson, et al. "Dose-efficient system for digital mammography", Proceedings of SPIE, Physics of Medical Imaging, vol. 3977, pp. 239-249 San Diego, 2000.

*Primary Examiner* — Taeho Jo
(74) *Attorney, Agent, or Firm* — Young & Thompson

(57) ABSTRACT

The proposed technology relates to an x-ray detector arrangement having x-ray detector sub-modules arranged in two or more layers, where the separation between adjacent sub-modules in a lower layer is smaller than the corresponding separation between sub-modules in an upper layer.

6 Claims, 5 Drawing Sheets

(56) References Cited

U.S. PATENT DOCUMENTS

| | | | | |
|---|---|---|---|---|
| 2007/0003006 A1* | 1/2007 | Tkaczyk | ............... | G01T 1/2985 378/19 |
| 2007/0206721 A1* | 9/2007 | Tkaczyk | ................ | A61B 6/032 378/19 |
| 2008/0061395 A1* | 3/2008 | Tkaczyk | ................ | A61B 6/032 257/443 |
| 2010/0187429 A1* | 7/2010 | Engel | .................... | G01T 1/2928 250/370.09 |
| 2010/0204942 A1* | 8/2010 | Danielsson | ............. | G01T 1/243 702/85 |
| 2010/0316184 A1* | 12/2010 | Iwanczyk | .............. | A61B 6/032 378/19 |
| 2012/0033785 A1* | 2/2012 | Michel | ............. | G01N 23/20075 378/21 |
| 2012/0145911 A1* | 6/2012 | Suyama | ............... | G01V 5/0041 250/366 |
| 2012/0153177 A1* | 6/2012 | Iwakiri | ................ | A61B 6/4291 250/370.09 |
| 2014/0037045 A1* | 2/2014 | Dafni | ...................... | A61B 6/032 378/5 |
| 2014/0110592 A1* | 4/2014 | Nelson | .................. | G01T 1/1611 250/370.09 |
| 2015/0124402 A1* | 5/2015 | Jang | ........................ | B32B 27/08 361/679.55 |
| 2015/0146844 A1* | 5/2015 | Zamyatin | ............... | A61B 6/032 378/5 |
| 2015/0323685 A1* | 11/2015 | Nelson | .................. | G01T 1/1611 250/370.08 |
| 2015/0331115 A1* | 11/2015 | Nelson | .................. | G01T 1/1611 250/363.03 |

* cited by examiner

X-RAY DETECTOR ARRANGEMENT

TECHNICAL FIELD

The present invention relates to x-ray detectors, and more specifically an x-ray detector arrangement having x-ray detector sub-modules arranged in two or more layers, as well as a corresponding x-ray imaging system.

BACKGROUND

Radiographic imaging such as x-ray imaging has been used for years in medical applications and for non-destructive testing.

Normally, an x-ray imaging system includes an x-ray source and an x-ray detector array consisting of multiple detectors comprising one or many detector elements (independent means of measuring x-ray intensity/fluence). The x-ray source emits x-rays, which pass through a subject or object to be imaged and are then registered by the detector array. Since some materials absorb a larger fraction of the x-rays than others, an image is formed of the subject or object.

An example of a commonly used x-ray imaging system is an x-ray Computed Tomography (CT) system, which may include an x-ray tube that produces a fan- or cone beam of x-rays and an opposing array of x-ray detectors measuring the fraction of x-rays that are transmitted through a patient or object. The x-ray tube and detector array are mounted in a gantry that rotates around the imaged object.

X-ray detectors made from low-Z materials such as Silicon need to have a substantial thickness in the direction of the x-ray beam in order to have sufficient detection efficiency to be used in CT. This can be solved by, for example, using an "edge-on" geometry, as in reference [1], in which the detector array is built up of a multitude of detectors, which comprise thin wafers of a low-atomic number material, oriented with the edge towards the impinging x-rays.

Examples of x-ray detectors with a low Z material such as Silicon can be found in references [1] and [2].

There is a general challenge in achieving a high detection efficiency, which translates into having a high fill factor and a high absorption efficiency (length in the direction of the impinging x-rays).

SUMMARY

It is a general object to provide an improved x-ray detector arrangement.

It is a specific object to increase the detection efficiency for such an x-ray detector arrangement.

It is also an object to provide an improved x-ray imaging system.

These and other objects are met by embodiments of the proposed technology.

According to an aspect of the proposed technology, there is provided an x-ray detector arrangement having x-ray detector sub-modules arranged in two or more layers,
wherein the separation between adjacent sub-modules in a lower layer is smaller than the corresponding separation between sub-modules in an upper layer.

In this way, the detection efficiency of the x-ray detector arrangement is increased by increasing the fill factor of the lower layer of detector sub-modules.

According to another aspect, there is provided an x-ray imaging system comprising such an x-ray detector arrangement.

Other advantages will be appreciated by reading the detailed description.

DETAILED DESCRIPTION

Figure 1A:
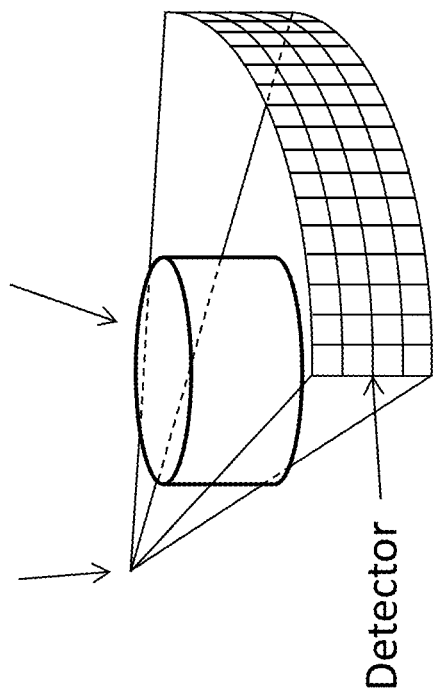
FIG. 1A is a schematic diagram illustrating an example of an x-ray imaging system such as a CT system.

FIG. 1A is a schematic diagram illustrating an example of an x-ray imaging system such as a CT system. The system basically includes an x-ray source and a detector, also referred to as an x-ray detector arrangement.

In 3D CT acquisition, x-ray projection measurements may for example be made along projection rays passing through a three-dimensional sub-volume of the object to be imaged. In 2D CT acquisition, the measurements are performed in one and the same plane through the object to be imaged. In 3D, the measurements are performed in different positions along a direction orthogonal to the plane in which the source-detector pair rotates.

Figure 1B:
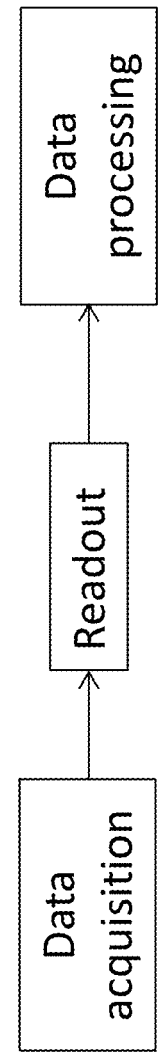
FIG. 1B is a schematic diagram illustrating an example of a related system for data acquisition and/or data read-out and/or data processing for an x-ray imaging system such as that of FIG. 1A.

FIG. 1B is a schematic diagram illustrating an example of a related system for data acquisition and/or data read-out and/or data processing for an x-ray imaging system such as that of FIG. 1A.

Figure 2:
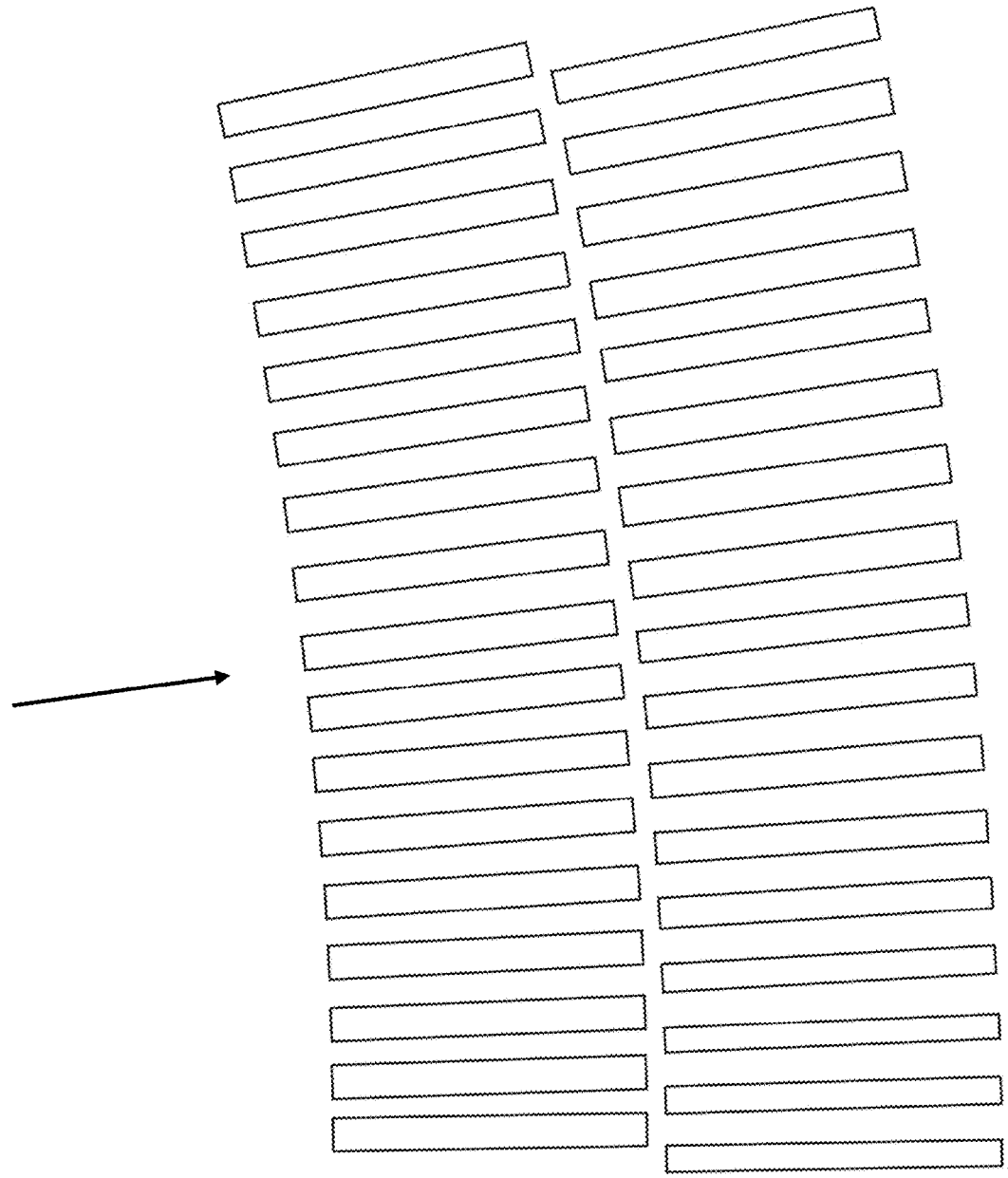
FIG. 2 is a schematic diagram illustrating a basic arrangement of x-ray detector sub-modules arranged in two layers.

An arrangement of x-ray detector sub-modules arranged in two layers is illustrated in the example of FIG. 2, similar to the configuration shown in reference [1].

Figure 3:
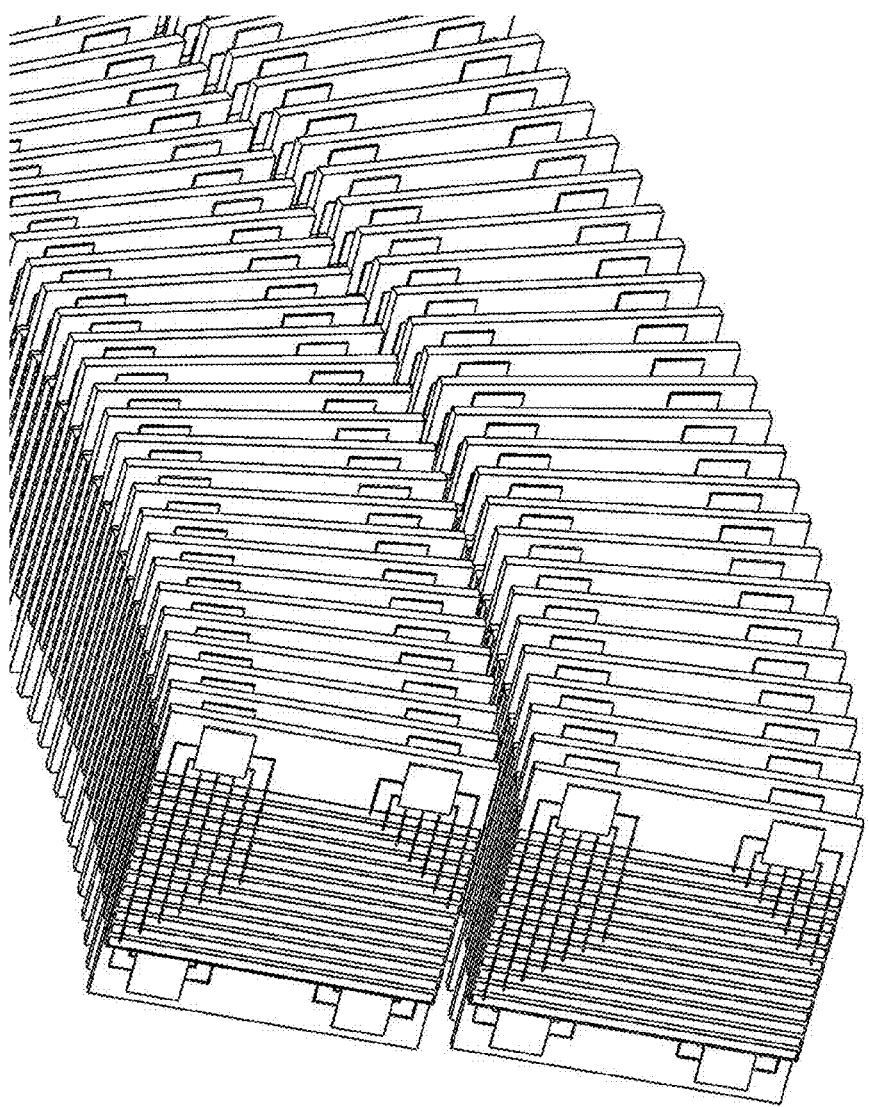
FIG. 3 is a schematic diagram illustrating a more detailed example of an x-ray detector arrangement comprising detector sub-modules in two layers.

FIG. 3 is a schematic diagram illustrating a more detailed example of an x-ray detector arrangement comprising detector sub-modules in two layers. In this particular example, the detector sub-modules are semiconductor detector modules using integrated circuits for data acquisition and/or readout, processing the electric charge generated from the x-ray(s) and converting it to digital data. The integrated circuits such as Application Specific Integrated Circuits (ASICs) are configured for connection to a digital data processing circuitry so the digital data may be sent to further digital data processing and/or memories and finally the data may be the input for reconstructing an image of an object.

Two detector layers is advantageous since there will be more space in between the detectors (sub-modules) for passive components and also this arrangement will allow air cooling of the sub-modules since the air can pass in between the sub-modules. Furthermore the risk for cross scatter is reduced since the scatter is depends on the total amount of detector volume in the vicinity and this is reduced by a factor two by having two layers (or possibly more layers).

A basic idea according to the proposed technology is to provide an x-ray detector arrangement having x-ray detector sub-modules arranged in two or more layers, wherein the separation between adjacent sub-modules in a lower layer is smaller than the corresponding separation between sub-modules in an upper layer.

In a first example, the width of the detector sub-modules in the lower layer may be larger than the width of the detector sub-modules in the upper layer.

In a second example, the lower layer may have a larger number of sub-modules than the upper layer.

The upper layer is generally arranged to be closer to the x-ray source than the lower layer.

By way of example, the detector sub-modules are detector modules oriented edge-on to the incoming x-rays.

As an example, the x-ray detector arrangement may preferably be at least partly based on Silicon as detector material.

In a particular example, each detector sub-module (or every second) has an anti-scatter foil attached to it and this is necessary to reduce scattered radiation in the detector but also to reduce scattered radiation from the object. These anti-scatter foils unfortunately reduce the geometrical efficiency since this is not active detector volume.

By way of example, the two-layer structure means the lower layer anti-scatter foils can be positioned under the top layer active detector area. This means increased geometrical efficiency and thus reduced radiation dose to the object.

As indicated, the two-layer structure (or more layers) means a possibility to increase detection efficiency by increasing the fill factor in a lower layer. One possibility is according to the examples of FIG. 4 or FIG. 5 by minimizing the separation between adjacent lower layer sub-modules. More specifically, the separation between adjacent lower layer sub-modules is smaller than the corresponding separation between upper layer sub-modules according to an example embodiment.

This can be done achieved by having a larger number of sub-modules in the bottom layer as illustrated with reference to the example of FIG. 4 or by increasing the width of the detector sub-modules in the bottom layer as explained with reference to the example of FIG. 5.

Figure 5:
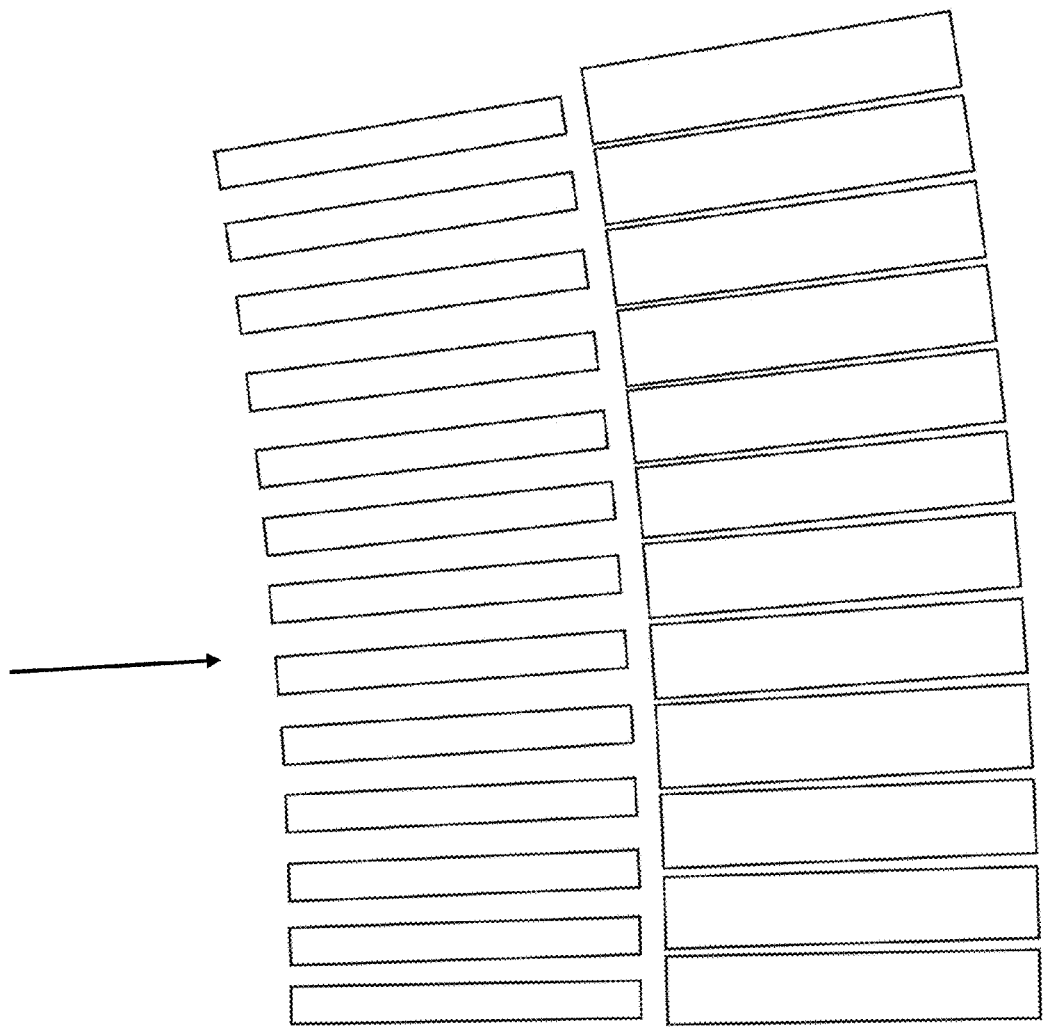
FIG. 5 is a schematic diagram illustrating another example of how to increase the fill factor in a lower layer of a multi-layered x-ray detector arrangement.

According to the example of FIG. 5 it is possible to increase the width of the detector sub-modules in the bottom layer. This means you would sacrifice some spatial resolution but the detection efficiency would be increased. More specifically, the width of the detector sub-modules in the bottom/lower layer is larger than the width of the detector sub-modules in the top/upper layer according to an example embodiment. Thereby the separation between adjacent bottom/lower layer sub-modules is smaller than the corresponding separation between top/upper layer sub-modules FIG. 2 shows an example of an arrangement of x-ray detector sub-modules in two layers. The top layer is matching the gaps in the bottom/lower layer and vice versa, which means that the x-rays (impinging from above) will encounter an even thickness of detector material. This means that the top/upper layer is typically closer to the x-ray source than the bottom/lower layer.

Figure 4:
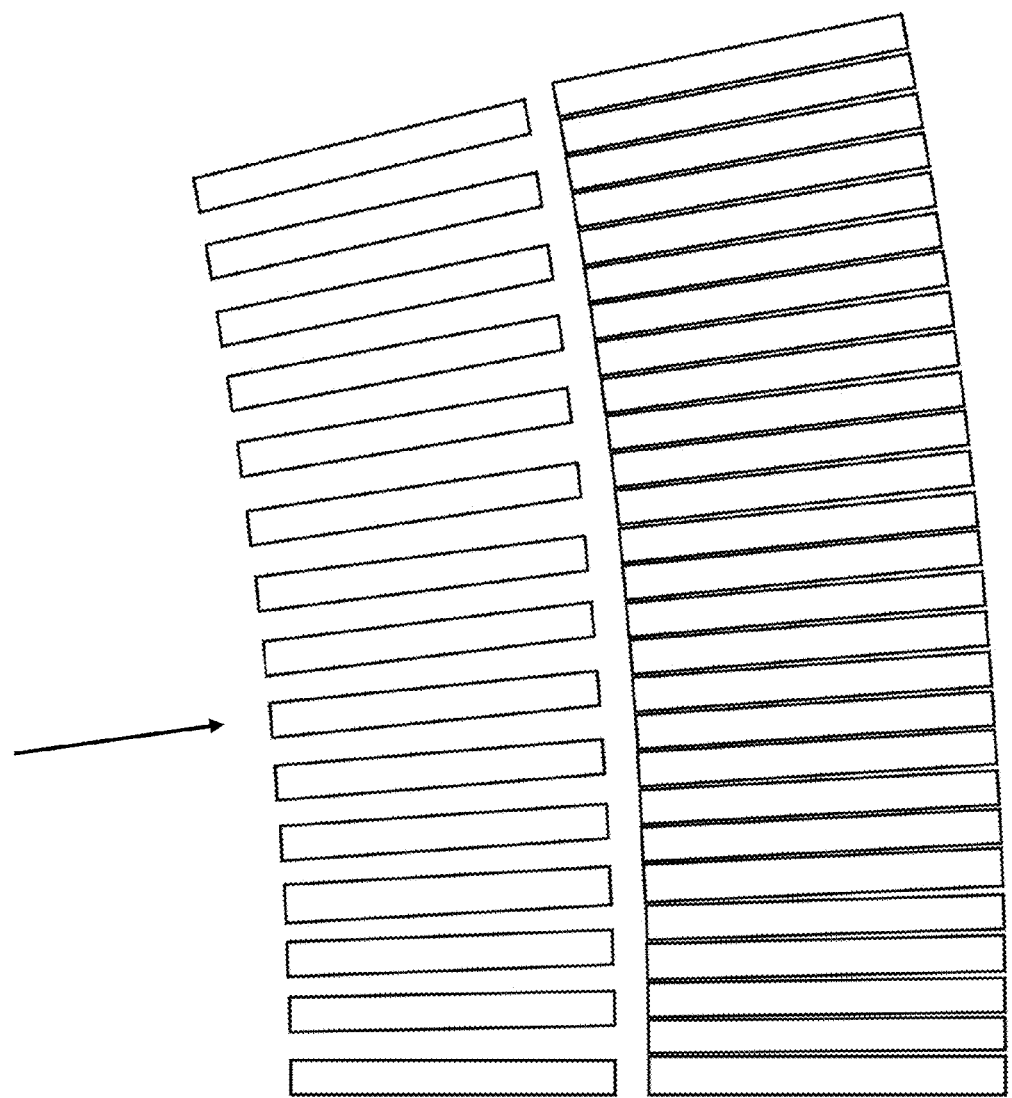
FIG. 4 is a schematic diagram illustrating an example of how to increase the fill factor in a lower layer of a multi-layered x-ray detector arrangement.

FIG. 4 displays an example of how the bottom/lower layer could have an increased fill factor of sub-modules. This would increase the production cost (since more sub-modules are required), but will increase the detection efficiency since a substantial number of the impinging x-rays will encounter double detector thickness, which will reduce the risk for an x-ray passing the two detector layers undetected. The arrangement could also increase spatial resolution since the two layers will be offset with a known distance and this can be used to optimize the sampling to avoid aliasing. It is not possible to have a 100% fill factor in the bottom/lower layer since there need to be space for integrated circuits for read-out of the data and anti-scatter foils.

FIG. 5 displays another example of how the bottom/lower layer could have an increased fill factor of sub-modules. In this case the width of the detector sub-modules is increased. This does not increase the production cost as much as when having many more sub-modules in the bottom layer. The drawback is that the spatial resolution in the bottom layer is slightly reduced. It is not possible to have a 100% fill factor in the bottom layer since there need to be space for integrated circuits for read-out of the data and anti-scatter foils.

The embodiments described above are merely given as examples, and it should be understood that the proposed technology is not limited thereto. It will be understood by those skilled in the art that various modifications, combinations and changes may be made to the embodiments without departing from the present scope as defined by the appended claims. By way of example, it will be appreciated that the arrangements described herein can be implemented, combined and re-arranged in a variety of ways. In particular, different part solutions in the different embodiments can be combined in other configurations, where technically possible.

REFERENCES

[1] U.S. Pat. No. 8,183,535
[2] M. Danielsson, H. Bornefalk, B. Cederström, V. Chmill, B. Hasegawa, M. Lundqvist, D. Nygren and T. Tabár, "Dose-efficient system for digital mammography", *Proc. SPIE, Physics of Medical Imaging*, vol. 3977, pp. 239-249 San Diego, 2000

The invention claimed is:

1. An x-ray detector arrangement having an x-ray detector array comprising multiple detectors, each detector being an x-ray detector sub-module comprising plural detector elements, wherein the x-ray detector x-ray detector sub-modules are arranged in two or more layers,
    wherein the separation between adjacent x-ray detector sub-modules in a lower layer is smaller than the corresponding separation between adjacent x-ray detector sub-modules in an upper layer, the upper layer being arranged to be closer to an x-ray source than the lower layer, wherein the upper layer has multiple x-ray detector sub-modules and the lower layer has multiple x-ray detector sub-modules, and the lower layer has a larger number of x-ray detector sub-modules than the upper layer and the lower layer thereby has an increased fill factor of x-ray detector sub-modules to increase detection efficiency, and
    wherein the x-ray detector sub-modules in the lower layer and the x-ray detector sub-modules in the upper layer have the same functionality and detect radiation in a same energy range.

2. The x-ray detector arrangement of claim 1, wherein the detector sub-modules are detector modules oriented edge-on to the incoming x-rays.

3. The x-ray detector arrangement of claim 1, wherein the x-ray detector arrangement is based on Silicon as detector material.

4. An x-ray imaging system comprising an x-ray detector arrangement according to claim 1.

5. The x-ray detector arrangement of claim 2, wherein the x-ray detector arrangement is based on Silicon as detector material.

6. An x-ray detector arrangement comprising:
   an x-ray detector array comprising plural detectors arranged with respect to a x-ray source, each detector being an x-ray detector sub-module comprising plural detector elements,
   wherein the x-ray detector sub-modules are arranged in an upper layer of N adjacent detector sub-modules and a lower layer of M adjacent detector sub-modules, M>N, the upper layer being arranged closer to the x-ray source than the lower layer, and
   wherein a separation between the M adjacent detector sub-modules in the lower layer is smaller than a corresponding separation between the N adjacent sub-modules in the upper layer, the lower layer thereby having an increased fill factor of the x-ray detector sub-modules that increases detection efficiency by having impinging x-rays encounter a double detector thickness which reduces a risk for an x-ray passing the upper and lower layers undetected, and
   wherein the x-ray detector sub-modules in the lower layer and the x-ray detector sub-modules in the upper layer have the same functionality and detect radiation in a same energy range.

\* \* \* \* \*